US008273378B2

(12) United States Patent
Riser et al.

(10) Patent No.: US 8,273,378 B2
(45) Date of Patent: *Sep. 25, 2012

(54) DIALYSIS SOLUTIONS CONTAINING PYROPHOSPHATES

(75) Inventors: Bruce L. Riser, Kenosha, WI (US); Paul Zieske, Glenview, IL (US); Sujatha Karoor, Lake Forest, IL (US); Himanshu D. Patel, Gurnee, IL (US)

(73) Assignees: Baxter International, Inc., Deerfield, IL (US); Baxter Healthcare S.A., Glattpark, (Opfikon) (CH)

( * ) Notice: Subject to any disclaimer, the term of this patent is extended or adjusted under 35 U.S.C. 154(b) by 283 days.

This patent is subject to a terminal disclaimer.

(21) Appl. No.: 12/687,536

(22) Filed: Jan. 14, 2010

(65) Prior Publication Data
US 2010/0119618 A1 May 13, 2010

Related U.S. Application Data

(63) Continuation of application No. 11/871,018, filed on Oct. 11, 2007, now Pat. No. 7,658,952.

(51) Int. Cl.
*A61K 33/42* (2006.01)
*A61K 31/045* (2006.01)
*A61K 31/19* (2006.01)
*A61K 31/70* (2006.01)
*A61K 33/00* (2006.01)
*A61K 47/00* (2006.01)
*A61P 7/08* (2006.01)

(52) U.S. Cl. ........ 424/603; 424/617; 424/677; 424/678; 424/679; 424/680; 424/681; 424/717; 424/722; 514/1.1; 514/23; 514/54; 514/60; 514/62; 514/557; 514/561; 514/738; 514/773; 514/777; 514/778; 514/784; 514/788

(58) Field of Classification Search .................. None
See application file for complete search history.

(56) References Cited

U.S. PATENT DOCUMENTS

| 3,931,396 | A | 1/1976 | Bardy et al. |
| 6,309,673 | B1 | 10/2001 | Duponchelle et al. |
| 6,537,976 | B1 | 3/2003 | Gupta |
| 6,689,275 | B1 | 2/2004 | Gupta |
| 6,779,468 | B1 | 8/2004 | Gupta |
| 7,658,952 | B2 * | 2/2010 | Riser et al. .................. 424/603 |
| 2005/0142212 | A1 | 6/2005 | Gupta |
| 2007/0012622 | A1 | 1/2007 | Wash |

FOREIGN PATENT DOCUMENTS

| WO | WO9829434 | 7/1998 |
| WO | WO 99/07419 | 2/1999 |
| WO | 0152647 | 7/2001 |
| WO | WO2005044189 | 5/2005 |
| WO | WO2006019843 | 2/2006 |
| WO | 2007016615 | 2/2007 |
| WO | 2007075877 | 7/2007 |
| WO | WO2007089571 | 8/2007 |
| WO | WO2007089577 | 8/2007 |

OTHER PUBLICATIONS

Lomashvili et al., "Phosphate-Induced Vascular Calcification: Role of Pryophosphate and Osteopontin," J Am Soc Nephrol, vol. 15 (2004) pp. 1392-1401.
Lomashvili et al., "Reduced Plasma Pyrophosphate Levels in Hemodialysis Patients," J Am Soc Nephrol vol. 16 (2005) pp. 2495-2500.
Fleisch et al., "Inhibition of Aortic Calcification by means of Pyrophosphate and Polyphosphates," Nature vol. 207 (1965); pp. 100-1301.
Crowther et al., "The Hydrolysis of the Condensed Phosphates I. Sodium Pyrophosphate and Sodium Triphosphate," Canadian Journal of Chemistry vol. 32 (1954); pp. 42-48.
Meyer et al., "Calcification Inhibitors in Rate and Human Serum and Plasma," Biochimica et Biophysica Acta, vol. 799 (1984) pp. 115-121.
El-Abbadi et al., "Arteriosclerosis, calcium phosphate deposition and cardiovascular disease in uremia: current concepts at the bench," Current Opinion in Nephrology and Hypertension vol. 14 (2005) pp. 519-524.
Towler, "Inorganic Pyrophosphate: A Paracrine Regulator of Vascular Calcification and Smooth Muscle Phenotype," Arterioscler. Thromb. Vasc. Biol. vol. 25 (2005) pp. 651-654.
Meyere, "Can Biological Calcification Occur in the Presence of Pyrophosphate?," Archives of Biochemistry and Biophysics, vol. 231, No. 1, May 15, 1984, pp. 1-8.
Terkeltaub, "Inorganic pyrophosphate generation and disposition in pathophysiology," Am J Physiol. Cell Physiol, vol. 281 (2001); pp. C1-C11.
Rufenacht et al., "Measurement of inhibitors of calcium phosphate precipitation in plasma ultrafiltrate," Am J Physiol vol. 246 (1984) pp. 648-655.
Tuchweber et al., "Effect of Sodium Pyrophosphate on Experimental Soft-Tissue Calcification and Hypercalcemia," Canadian Journal of Physiology and Pharmacology, vol. 45 (1967); pp. 957-964.
Russell et al., "Inorganic Pyrophosphate and Pyrophosphatases in Calcification and Calcium Homeostasis," Clinical Orthopaedics and Related Research No. 69 (1970); pp. 101-117.
Fleisch et al. "Diphosphonates Inhibit Formation of Calcium Phosphate Crystals in vitro and Pathological Calcification in vivo," Science vol. 165, (1969) pp. 1264-1266.
Francis, "Diphosphonates Inhibit Hydroxyapatite Dissolution in vitro and Bone Resportion in Tissue Culture and in vivo," Science vol. 165 (1969) pp. 1262-1264.

(Continued)

*Primary Examiner* — Johann Richter
*Assistant Examiner* — Frank Choi
(74) *Attorney, Agent, or Firm* — K&L Gates LLP

(57) ABSTRACT

Dialysis solutions comprising pyrophosphates and methods of making and using the dialysis solutions are provided. In an embodiment, the present disclosure provides a dialysis solution comprising a stable and therapeutically effective amount of pyrophosphate. The dialysis solution can be sterilized, for example, using a technique such as autoclave, steam, high pressure, ultra-violet, filtration or combination thereof. The dialysis solution can be in the form of a concentrate.

26 Claims, No Drawings

OTHER PUBLICATIONS

Rodan et al. "Bisphosphonates: Mechanisms of Action," J. Clin. Invest.—The American Society for Clinical Investigation, Inc. vol. 97, No. 12 (1996), pp. 2692-2696.

Fleisch, "Bisphosphonates: Mechanisms of Action," Endocrine Reviews vol. 19(1) (1998)—Downloaded from edrv.endojournals. org on Jun. 28, 2006.

Nitta et al., "Effects of Cyclic Intermittent Etidronate Therapy on Coronary Artery Calcification in Patients Receiving Long-Term Hemodialysis," American Journal of Kidney Diseases vol. 44, No. 4 (2004) pp. 680-688.

International Search Report dated Jan. 13, 2009, 8 pages.

Written Opinion of the International Searching Authority dated Jan. 13, 2009, 8 pages.

Search Report—Intellectual Property Office of Singapore—Application No. 201002467-7—mailing date Jul. 7, 2011, 9 pages.

* cited by examiner

DIALYSIS SOLUTIONS CONTAINING PYROPHOSPHATES

CROSS-REFERENCE TO RELATED APPLICATIONS

This application is a continuation of U.S. patent application Ser. No. 11/871,018, filed Oct. 11, 2007, now U.S. Pat. No. 7,658,952, the entire content of which is expressly incorporated herein by reference.

BACKGROUND

The present disclosure relates generally to medical treatments. More specifically, the present disclosure relates to solutions used for dialysis therapy.

Due to disease, insult or other causes, a person's renal system can fail. In renal failure of any cause, there are several physiological derangements. The balance of water, minerals and the excretion of daily metabolic load are no longer possible in renal failure. During renal failure, toxic end products of nitrogen metabolism (e.g., urea, creatinine, uric acid and others) can accumulate in blood and tissues.

Kidney failure and reduced kidney function have been treated with dialysis. Dialysis removes waste, toxins and excess water from the body that would otherwise have been removed by normal functioning kidneys. Dialysis treatment for replacement of kidney functions is critical to many people because the treatment is life saving. One who has failed kidneys could not continue to live without replacing at least the filtration functions of the kidneys.

Past studies have shown that end stage renal disease (ESRD) patients are deficient in pyrophosphate. For example, pyrophosphate is thought to be instrumental in prevention of calcification of soft tissues and pyrophosphate deficiencies may be a risk factor in calciphylaxis. Plasma and cell bound (erythrocyte) pyrophosphate is reduced approximately 30% in dialysis patents over normal individuals even though the kidney that normally clears pyrophosphate from circulation is not functioning. These levels are below those previously shown to prevent vascular calcification of vessels in culture. Replacement of pyrophosphate in dialysis patients may inhibit the formation of calcium deposits in vessels and thus vascular calcification. Therefore, stable dialysis solutions containing this compound may be highly beneficial.

SUMMARY

The present disclosure relates generally to dialysis solutions and methods of making and using same. More specifically, the present disclosure relates to dialysis solutions comprising a stable and therapeutically effective amount of pyrophosphates. For example, the dialysis solutions can be suitable for peritoneal dialysis and/or hemodialysis to replace deficient amounts or add therapeutically effective amounts of pyrophosphate. The dialysis solutions can be used, for example, as a single dialysis solution in a single container or as a dialysis part of a separately housed or multi-chambered container.

In an embodiment, the present disclosure provides a dialysis solution comprising a therapeutically effective amount of pyrophosphate. The dialysis solution can be sterilized, for example, using a technique such as autoclave, steam, high pressure, ultra-violet light, filtration or combination thereof. The dialysis solution can be in the form of one or more concentrates that can be combined to form a final dialysis solution. The dialysis solutions/concentrates can be specifically formulated so that the pyrophosphate in the dialysis solution remains stable (e.g. does not degrade) during the sterilizing and over extended periods of time (e.g. during storage).

In another embodiment, the present disclosure provides a peritoneal dialysis solution comprising a therapeutically effective amount of pyrophosphate, an osmotic agent, a buffer and an electrolyte. For example, the osmotic agent can comprise glucose, glucose polymers (e.g. maltodextrin, icodextrin), glucose polymer derivatives, cyclodextrins, modified starch, hydroxyethyl starch, polyols, fructose, amino acids, peptides, proteins, amino sugars, glycerol, N-acetyl glucosamine (NAG) or combination thereof The buffer can comprise bicarbonate, lactate, pyruvate, acetate, citrate, tris (i.e. trishydroxymethylaminomethane), amino acids, peptides or combination thereof The electrolytes can comprise sodium, potassium, magnesium, calcium and chloride.

In an alternative embodiment, the present disclosure provides a dialysis solution comprising two or more separate dialysis parts (e.g. individual concentrates) with each dialysis part comprising one or more dialysis components, for example, that are combined and administered to a patient. A first dialysis part comprises an osmotic agent and a second dialysis part comprises a buffer. At least one of the first and second dialysis parts comprises one or more electrolyte salts and pyrophosphate.

In yet another embodiment, the present disclosure provides a method of making a multi-part dialysis solution. The method comprises providing two or more dialysis parts with each dialysis part comprising one or more dialysis components such as an osmotic agent, a buffer, an electrolyte or combination thereof. The pyrophosphate is added to at least one of the dialysis parts and sterilized with the dialysis part. The sterilizing can be performed, for example, using heat (e.g. steam), high pressure, ultra-violet light or filtration. The dialysis parts are mixed to form the final dialysis solution.

In an alternative embodiment, the present disclosure provides a method of providing dialysis such as peritoneal dialysis or hemodialysis to a patient in need of same. The method comprises administering a sterilized dialysis solution to the patient. The dialysis solution comprises an osmotic agent, an electrolyte, a buffer and pyrophosphate. In another embodiment, the method comprises providing two or more separately housed dialysis parts with each part comprising one or more dialysis components such as, for example, an osmotic agent, a buffer, an electrolyte and combinations thereof. At least one of the dialysis parts comprises pyrophosphate. One or more of the dialysis parts are sterilized. The dialysis parts are then mixed to form a resultant sterilized dialysis solution, and the sterilized dialysis solution is administered to the patient. The mixing can be performed onsite by a mixing system or by the patient or healthcare worker.

In yet another embodiment, the present disclosure provides a method of treating a dialysis patient. The method comprises providing a sterilized dialysis solution comprising a therapeutically effective amount of pyrophosphate to a dialysis patient having vascular calcification.

An advantage of the present disclosure is to provide improved dialysis solutions.

Another advantage of the present disclosure is to provide sterilized dialysis solutions comprising pyrophosphate.

Yet another advantage of the present disclosure is to provide improved methods of providing dialysis to patients.

Still another advantage Of the present disclosure is to provide improved methods of making dialysis solutions.

Another advantage of the present disclosure is to provide ready to use sterilized dialysis solutions comprising a stable amount of pyrophosphates.

Yet another advantage of the present disclosure is to provide ready to use sterilized dialysis solutions comprising a therapeutically effective amount of pyrophosphates.

Furthermore, an advantage of the present disclosure is to provide improved treatments for patients requiring dialysis.

Additional features and advantages are described herein, and will be apparent from, the following Detailed Description.

DETAILED DESCRIPTION

The present disclosure generally relates to dialysis solutions and methods of making and using same. More specifically, the present disclosure relates to dialysis solutions comprising pyrophosphates and methods of making and using the dialysis solutions. For example, the dialysis solutions in embodiments of the present disclosure are designed to reduce or prevent vascular calcification due to pyrophosphate deficiencies in patients who are undergoing dialysis therapies. In addition, the amount of pyrophosphate can remain stable (e.g. not readily degrade) in the dialysis solutions before, during or after sterilization or over a specific amount of time (e.g. during storage).

In a general embodiment, the present disclosure provides a dialysis solution or dialysis concentrate comprising one or more dialysis components (e.g. ingredients or constituents of a dialysis solution) and a stable and therapeutically effective amount of pyrophosphate. The dialysis solutions can be suitable for peritoneal dialysis, hemodialysis or any other dialysis therapies. In an embodiment, the dialysis solution comprises from about 0.1 µM to about 1000 µM of pyrophosphate. In another embodiment, the dialysis solution comprises from about 1 µM to about 15 µM of pyrophosphate. The dialysis solutions in alternative embodiments of the present disclosure can be used, for example, as a single dialysis solution in a single container or as a dialysis part of a separately housed or multi-chambered container.

In alternative embodiments, the present disclosure provides dialysis solutions/concentrates comprising pyrophosphates that are stable under sterilization conditions. For example, it has been surprisingly found that heat sterilizing dialysis solutions comprising pyrophosphates at a higher pH (e.g. above 6) and using specific dialysis components such as buffers reduces the amount of pyrophosphate degradation during the sterilization. Moreover, non-heat sterilization methods such as high pressure, ultra-violet or filtration provide sterilized dialysis solutions comprising a stable amount of pyrophosphates at lower pHs (e.g. below 6). As a result, a greater amount of the original pyrophosphate remains in the sterilized dialysis solutions, which can be stored for later use.

The dialysis solutions can be sterilized using any suitable sterilizing technique such as, for example, autoclave, steam, high pressure, ultra-violet, filtration or combination thereof. The dialysis solutions can also be sterilized before, during or after one or more dialysis components and one or more pyrophosphates are combined.

The pyrophosphates can be, for example, pyrophosphoric acid, salts of pyrophosphate or combinations thereof Salts of pyrophosphates comprise sodium pyrophosphate, potassium pyrophosphate, calcium pyrophosphate, magnesium pyrophosphate, etc. The dialysis components can be any one or more of osmotic agents, buffers, electrolytes or combination thereof as discussed in detail below.

The dialysis solution can also comprise one or more electrolytes in the following ranges from: about 100 to about 140 mEq/L of $Na^+$, about 70 to about 130 mEq/L of $Cl^-$, 0.1 to about 4 mEq/L of $Ca^{2+}$, 0.1 to about 4 mEq/L of $Mg^{2+}$ and/or 0.1 to about 4 mEq/L of $K^+$.

In another embodiment, the dialysis solution/concentrate can comprise two or more dialysis parts (e.g. individual solutions/concentrates that make up the final dialysis solution when mixed) with each dialysis part comprising one or more dialysis components. The pyrophosphate can be added to one or more of the dialysis parts and sterilized with the dialysis part. The two or more dialysis parts can be stored and sterilized separately, for example, in separate containers or a multi-chamber container.

A variety of different and suitable acidic and/or basic agents can be utilized to adjust the pH of the osmotic, buffer and/or electrolyte solutions or concentrates. For example, a variety of inorganic acids and bases can be utilized including hydrochloric acid, sulfuric acid, nitric acid, hydrogen bromide, hydrogen iodide, sodium hydroxide, the like or combination thereof In another embodiment, the present disclosure provides a multi-part dialysis solution comprising at least a first dialysis part comprising an osmotic agent and a second dialysis part comprising a buffer. One or more of the separate dialysis parts comprises an electrolyte. In an embodiment, the pH of the first dialysis part ranges between about 2 to about 6. In alternative embodiments, the pH of the first dialysis part ranges between about 2 to about 2.5, between about 3 to about 3.5 and between about 4 to about 4.5. The electrolytes can be balanced between the first dialysis part and the second dialysis part. In an embodiment, the second dialysis part comprises the therapeutically effective amount of pyrophosphate. The first and second dialysis parts can include a variety of other suitable dialysis components to ensure that the first and second parts can be, for example, readily and sterilely mixed to form ready-to-use dialysis formulations, which can then be administered to a person in need of same.

Additional ready-to-use formulations in embodiments of the present disclosure can be prepared in a number of suitable ways. In an embodiment, first and second (or more) individual parts of a dialysis solution are separately stored from each other, such as in separate and hydraulically connected chambers of a multi-chamber container, until mixed together to form a mixed solution. In this regard, the ready-to-use formulation can be prepared within the container by mixing its separate dialysis parts within the container. This can effectively eliminate the need to manually inject all or at least a portion of the dialysis parts into the container to form the mixed solution, thus ensuring that the ready-to-use formulation can be readily prepared under sterile conditions.

Further, the container can be configured such that one of the dialysis parts can be placed in direct fluid communication with the patient prior to mixing while the other part cannot be placed in direct fluid communication with the patient prior to mixing. This can provide an added level of safety with respect to the preparation and administration of the ready-to-use formulation of the present disclosure as the single part that cannot be placed in direct fluid communication with the patient physically cannot be fed to the patient unless it is first mixed with the other part. In this regard, if, by chance, the single dialysis part that physically cannot be placed in direct fluid communication with the patient were to have an undesirable concentration of dialysis components such as potassium, sodium or the like, this configuration would necessarily ensure that the undesirable level of constituents is not fed or administered to the patient.

In an alternative embodiment, the present disclosure provides a peritoneal dialysis solution comprising a stable and therapeutically effective amount of pyrophosphate, an osmotic agent, a buffer and an electrolyte. For example, the osmotic agent can comprise glucose, glucose polymers, glucose polymer derivatives, cyclodextrins, modified starch, hydroxyethyl starch, polyols, fructose, amino acids, peptides, proteins, amino sugars, glycerol, N-acetyl glucosamine (NAG) or combination thereof. The buffer can comprise bicarbonate, lactate, pyruvate, acetate, citrate, tris (i.e. trishydroxymethylaminomethane), amino acids, peptides or combination thereof. The electrolytes can comprise sodium, potassium, magnesium, calcium and chloride. The peritoneal dialysis solution comprising a therapeutically effective amount of pyrophosphate can be sterilized in any suitable manner such as, for example, heat sterilization.

It should be appreciated that the individual dialysis parts of the multi-part dialysis solutions can be housed or contained in any suitable manner such that the dialysis solutions can be effectively prepared and administered. A variety of containers can be used to house the two or more dialysis parts, such as separate containers (e.g., flasks or bags) that are connected by a suitable fluid communication mechanism. The two or more separate parts of a dialysis solution can be separately sterilized and stored in the containers. The pyrophosphates can be added to at least one of the dialysis parts and sterilized with that dialysis part. The dialysis part not containing pyrophosphates can also be sterilized.

In an embodiment, the dialysis parts can be stored separately, for example, in separate compartments or chambers of the same container (e.g. of a multi- or twin-chambered bag) and combined prior to or during dialysis treatment. An activation of a barrier such as, for example, a peel seal or frangible between the chambers can allow for mixing of the contents of both chambers. The container can be covered with a gas impermeable outer-container. Alternatively, the sterilized dialysis parts can be combined at any time to form a complete ready-to-use dialysis solution as previously discussed.

In still another embodiment, the present disclosure provides a method of making a stable multi-part dialysis solution comprising pyrophosphate. The method comprises providing two or more dialysis parts with each part comprising one or more dialysis components such as an osmotic agent, a buffer or an electrolyte. Pyrophosphate is added to one or more of the dialysis parts and sterilized with the dialysis part. The dialysis parts are mixed to form the final dialysis solution. The sterilization can be performed, for example, by autoclave, steam, high pressure, ultra-violet, filtration or combination thereof. The sterilizing can be performed at a temperature and a pH that does not result in significant breakdown of the pyrophosphate in the dialysis solution. For example, a suitable buffer can be used to maintain the pH at a level that minimizes pyrophosphate degradation. In an alternative embodiment, the method comprises preparing a single dialysis solution comprising one or more of an osmotic agent, an electrolyte and a buffer along with pyrophosphate and sterilizing the dialysis solution.

In an embodiment, the pH of the dialysis solution or individual dialysis part comprising the pyrophosphate is 6 or greater during the sterilization. In another embodiment, the pH of the dialysis solution or individual dialysis part comprising the pyrophosphate is 7 or greater during the sterilization. In an alternative embodiment, the pH of the dialysis solution or individual dialysis part comprising the pyrophosphate is 8 or greater during the sterilization. In yet another embodiment, the pH of the dialysis solution or individual dialysis part comprising the pyrophosphate is 9 or greater during the sterilization. Preferably, the dialysis solution or dialysis part comprising the pyrophosphate also contains a suitable buffer during sterilization.

In an alternative embodiment, the present disclosure provides a method of providing dialysis to a patient in need of same. For example, the patient may have or be prone to vascular calcification or have a phosphate or pyrophosphate deficiency. The method comprises administering a sterilized dialysis solution to the patient. The dialysis solution comprises one or more of an osmotic agent, an electrolyte and a buffer along with pyrophosphate. In an embodiment, the pyrophosphate can be administered to the patient in an amount from about 0.01 µM/day to about 20 mM/day.

In an alternative embodiment, the present disclosure provides a method for providing dialysis to a patient. The method comprises providing two or more separately housed dialysis parts with each part comprising a dialysis component such as, for example, an osmotic agent, a buffer, an electrolyte and combinations thereof. At least one of the dialysis parts comprises pyrophosphate. One or more of the dialysis parts are sterilized using any suitable sterilization technique. The dialysis parts are then mixed to form a resultant sterilized dialysis solution, and the sterilized dialysis solution is administered to the patient. The mixing can be performed onsite by any suitable mixing system or by the patient or healthcare provider. For example, the dialysis parts can be stored in separate chambers of a container, and barrier(s) such as, for example, a peel seal or frangible between the chambers can be broken to allow the parts to mix.

In addition to the pyrophosphates as previously discussed, the sterilized dialysis solutions and individual dialysis parts of the present disclosure can include any suitable number, type and amount of dialysis components that are typically used as part of, or during, dialysis treatments. By way of example, the dialysis components can comprise one or more suitable osmotic agents, buffers, electrolytes and combinations thereof. Examples of osmotic agents include glucose, glucose polymers (e.g. maltodextrin, icodextrin), glucose polymer derivatives, cyclodextrins, modified starch, hydroxyethyl starch, polyols (e.g. xylitol), fructose, amino acids, peptides, proteins, amino sugars, glycerol, N-acetyl glucosamine (NAG) and/or the like and combinations thereof. Examples of the buffers include bicarbonate, lactic acid/lactate, pyruvic acid/pyruvate, acetic acid/acetate, citric acid/citrate, tris, amino acids, an intermediate of the KREBS cycle and/or the like and combinations thereof Examples of electrolytes include calcium, magnesium, sodium, potassium, chloride and/or the like and combinations thereof.

The peritoneal dialysis solutions can preferably contain a dialysis component such as an osmotic agent to maintain the osmotic pressure of the solution greater than the physiological osmotic pressure (e.g. greater than about 285 mOsmol/kg). For example, glucose can be a preferred osmotic agent because it provides rapid ultrafiltration rates. Other suitable types of osmotic agents such as amino acids can be used in addition to or as a substitute for glucose. The dialysis solution can be subsequently sterilized after the osmotic agent and the pyrophosphates are combined.

Another family of compounds capable of serving as osmotic agents in peritoneal dialysis solutions is that of glucose polymers or their derivatives, such as icodextrin, maltodextrins, hydroxyethyl starch and the like. While these compounds are suitable for use as osmotic agents, they can be sensitive to low and high pH, especially during sterilization and long-term storage. Glucose polymers, such as icodextrin, can be used in addition to or in place of glucose in peritoneal dialysis solutions. In general, icodextrin is a polymer of glucose derived from the hydrolysis of corn starch. It has a molecular weight of 12-20,000 Daltons. The majority of glucose molecules in icodextrin are linearly linked with $\alpha$(1-4) glucosidic bonds (>90%) while a small fraction (<10%) is linked by $\alpha$(1-6) bonds.

The sterilized dialysis solutions of the present disclosure can be used in a variety of suitable applications. For example, the dialysis solutions can be used during peritoneal dialysis, such as automated peritoneal dialysis, continuous ambulatory peritoneal dialysis, continuous flow peritoneal dialysis and the like. It should be appreciated that the present disclosure can be used in a variety of different and suitable dialysis therapies to treat kidney failure.

Although the present disclosure, in an embodiment, can be utilized in methods providing a dialysis therapy for patients having chronic kidney failure or disease, it should be appreciated that the present disclosure can be used for acute dialysis needs, for example, in an emergency room setting. Lastly, as one of skill in the art appreciates, the intermittent forms of therapy (e.g., hemofiltration, hemodialysis, peritoneal dialysis and hemodiafiltration) may be used in the in center, self/limited care as well as the home settings.

The dialysis components can also comprise bicarbonates and acids. The bicarbonates can comprise an alkaline solution such that the bicarbonate can remain stable without the use of a gas barrier overpouch or the like. The individual bicarbonate solution can have a pH that ranges from above about 8.6, preferably about 9. The pH of the bicarbonate solution part can be adjusted with any suitable type of ingredient, such as sodium hydroxide and/or the like. Illustrative examples of the bicarbonate solution of the present disclosure can be found in U.S. Pat. No. 6,309,673, entitled BICARBONATE-BASED SOLUTION IN TWO PARTS FOR PERITONEAL DIALYSIS OR SUBSTITUTION IN CONTINUOUS RENAL REPLACEMENT THERAPY, issued on Oct. 30, 2001, the disclosure of which is herein incorporated by reference.

The acids can comprise one or more physiological acceptable acids, such as lactic acid, pyruvic acid, acetic acid, citric acid, hydrochloric acid and the like. The acids can be in an individual solution having a pH that ranges from about 5 or less, about 4 or less, about 3 or less, about 2 or less, about 1 or less, and any other suitable acidic pH. The use of an organic acid, such as lactic acid, alone or in combination with another suitable acid, such as a suitable inorganic acid including hydrochloric acid, another suitable organic acid (e.g. lactic acid/lactate, pyruvic acid/pyruvate, acetic acid/acetate, citric acid/citrate) and the like in the acid solution can make the solution more physiologically tolerable according to an embodiment.

It should be appreciated that the dialysis solutions of the present disclosure can include any other suitable components/ingredients for dialysis treatment in addition to those components described above. In an embodiment, the pH of the (mixed) dialysis solutions can have a broad range, preferably between about 4 to about 9. In another embodiment, the pH of the (mixed) dialysis solutions can have a broad range, preferably between about 5 to about 8.

EXAMPLES

By way of example and not limitation, the following examples are illustrative of various embodiments of the present disclosure and further illustrate experimental testing conducted with dialysis solutions comprising pyrophosphates.

Example 1

Pyrophosphate Stability in Dialysis Solutions

Dianeal® and Physioneal® peritoneal dialysis (PD) solutions (Baxter Healthcare Corporation) containing disodium pyrophosphate salt served as the test articles for this study.

A stock solution of 2.5 millimolar (mM) solution of pyrophosphate (PPi) was prepared using disodium pyrophosphate salt and deionized water free of carbon dioxide. Predetermined volume amounts of this stock solution were diluted to 1-L with individual volume of PD solutions to generate 1-L solutions containing PPi (see Table 1) in a "ready-to-use" product.

For each test sample (i.e. 1 L PD solution with PPi), aliquots were placed into autoclavable Pyrex® bottles. The remaining solution volume for each test samples was reserved for analysis as T=0.

Data Analysis

The study evaluated changes in pyrophosphate concentrations upon steam sterilization in different autoclaves and with different sterilization times. PPi analysis was performed using a modified ion chromatographic method. The method provides results in parts per million (ppm). Results for PPi levels in the test samples contained in Table 1 were converted from ppm and are reported in micromoles per liter ($\mu$mol/L) and percent recovery (of initial) pyrophosphate (% PPi).

TABLE 1

Recovery of Pyrophosphate in PD Solutions Before and after Steam Sterilization

| Sample | Time Zero | | |
|---|---|---|---|
| | Expected | Observed | % Recovery |
| US-NaPyro-Dianeal | 0.100 | 0.093 | 93 |
| US-NaPyro-Physioneal | 0.200 | 0.209 | 105 |
| S-NaPyro-Dianeal Sol-1 Autoclave-A (30 min) | 0.100 | 0.023 | 23 |
| S-NaPyro-Dianeal Sol-2 Autoclave-A (30 min) | 0.100 | | |
| S-NaPyro-Dianeal Sol-1 Autoclave-B (30 min) | 0.100 | 0.000 | 0 |
| S-NaPyro-Dianeal Sol-2 Autoclave-B (30 min) | 0.100 | | |
| S-NaPyro-Dianeal Sol-1 Autoclave-A (40 min) | 0.100 | 0.022 | 22 |
| S-NaPyro-Dianeal Sol-2 Autoclave-A (40 min) | 0.100 | | |
| S-NaPyro-Dianeal Sol-1 Autoclave-B (40 min) | 0.100 | 0.000 | 0 |
| S-NaPyro-Dianeal Sol-2 Autoclave-B (40 min) | 0.100 | | |
| S-NaPyro-Physio Buffer Sol-1 Autoclave A (30 min) | 0.200 | 0.191 | 95 |
| S-NaPyro-Physio Buffer Sol-2 Autoclave A (30 min) | 0.200 | | |
| S-NaPyro-Physio Buffer Sol-1 Autoclave B (30 min) | 0.200 | 0.182 | 91 |
| S-NaPyro-Physio Buffer Sol-2 Autoclave B (30 min) | 0.200 | | |

TABLE 1-continued

Recovery of Pyrophosphate in PD Solutions Before and after Steam Sterilization

| | Time Zero | | |
|---|---|---|---|
| Sample | Expected | Observed | % Recovery |
| S-NaPyro-Physio Buffer Sol-1 Autoclave A (40 min) | 0.200 | 0.186 | 93 |
| S-NaPyro-Physio Buffer Sol-2 Autoclave A (40 min) | 0.200 | | |
| S-NaPyro-Physio Buffer Sol-1 Autoclave B (40 min) | 0.200 | 0.173 | 86 |
| S-NaPyro-Physio Buffer Sol-2 Autoclave B (40 min) | 0.200 | | |

*Reported values for sterilized are averages of replicates
US—Unsterilized samples
S—Sterilized samples The results demonstrate:
Steam sterilized test samples of Dianeal® with PPi show a decrease in PPi concentration.
Steam sterilized samples of Physioneal® Buffer with PPi show a small change in PPi level. This stability may be attributed to high pH conditions of the test sample compared with Dianeal®.

Example 2

Effect of Buffer on Pyrophosphate Stability

Introduction: This study was designed to evaluate the stability of pyrophosphate salts with different buffers over a pH range from 4 to 10 during steam sterilization and after storage at 40° C. Two pyrophosphate salts and four buffers were obtained for the study. TRIS was added to all solutions as a pH stabilizer. Two of the solutions were also prepared without TRIS for comparison. The pH of the solutions was adjusted from pH 4-10 with 1N HCl or 1N NaOH. The solutions were sterilized at 121° C. for 40 minutes. Pyrophosphate concentration was determined before and after sterilization and after storage. The pH was also determined after sterilization and after storage.

The salts tested were:
1. Disodium Pyrophosphate ($Na_2H_2P_2O_7$)
2. Tetrapotassium Pyrophosphate ($K_4P_2O_7$)

The study was performed using the sodium and potassium salts of pyrophosphate with the buffers shown below. Solutions were not prepared with bicarbonate below pH 7 because bicarbonate will decompose at a lower pH.
1. Sodium Lactate
2. Sodium Bicarbonate
3. Sodium Citrate
4. Sodium Pyruvate The concentrations of the solution components are shown below in Table 2.

TABLE 2

| Components | Concentration |
|---|---|
| PPi Salts | 0.2 mM |
| NaCl | 90 mM |
| Buffers | 40 mM |
| TRIS | 10 mM |

Results and Discussions
The results of this study are summarized in the following four tables:

TABLE 3

Recoveries for Disodium Pyrophosphate (Unsterilized)

| pH | Sod. Lac | Sod. Lac N/TRIS | Sod. BiC | Sod. BiC N/TRIS | Citrate | Pyruvate |
|---|---|---|---|---|---|---|
| 4 | 98 | 90 | N/A | N/A | 81 | 97 |
| 5 | 102 | 97 | N/A | N/A | 89 | 98 |
| 6 | 103 | 98 | N/A | N/A | 95 | 98 |
| 7 | 104 | 97 | 96 | 95 | 99 | 99 |
| 8 | 105 | 98 | 98 | 96 | 99 | 100 |
| 9 | 104 | 98 | 98 | 97 | 100 | 100 |
| 10 | 104 | 98 | 97 | 95 | 98 | 100 |

Reported values are the % recovery of the pyrophosphate
Values are rounded to the nearest whole numbers.
Results obtained before sterilization.
N/A = not applicable
N/TRIS = No Tris Unsterilized Disodium Pyrophosphate (Table 3):
Recoveries were 95% or greater for all buffers at pH 6 and higher.
The recoveries with citrate at pH 4 and 5 were 81% and 89%, respectively, and ranged from 90-102% in the other buffers at this low pH range.
There is no difference in recovery between bicarbonate with or without TRIS, and with lactate values are similar, or slightly higher, with TRIS.

TABLE 4

Recoveries of Disodium Pyrophosphate (sterilized) at Time Zero and after Storage at 40° C.

| pH | Sod. Lac | Sod. Lac N/TRIS | Sod. BiC | Sod. BiC N/TRIS | Citrate | Pyruvate |
|---|---|---|---|---|---|---|
| 4 | 9 | 0 | N/A | N/A | 9 | 8 |
| 5 | 9 | 10 | N/A | N/A | 9 | 9 |
| 6 | 10 | 13 | N/A | N/A | 17 | 9 |
| 7 | 10 (11) [11] | 33 (23) [23] | 52 (51) [51] | 71 (66) [70] | 35 (35) | 9 (12) |
| 8 | 14 (14) [15] | 42 (39) [39] | 73 (72) [71] | 84 (81) [83] | 47 (47) | 14 (17) |

TABLE 4-continued

Recoveries of Disodium Pyrophosphate (sterilized)
at Time Zero and after Storage at 40° C.

| pH | Sod. Lac | Sod. Lac N/TRIS | Sod. BiC | Sod. BiC N/TRIS | Citrate | Pyruvate |
|---|---|---|---|---|---|---|
| 9 | 54 (47) [50] | 58 (53) [53] | 94 (94) [92] | 92 (88) [91] | 73 (73) | 51 (56) |
| 10 | 84 (80) [80] | 71 (68) [66] | 99 (98) [97] | 97 (94) [97] | 86 (86) | 84 (89) |

Reported values are the % recovery of the pyrophosphate
Values are rounded to the nearest whole numbers.
Samples sterilized at 121 C. for 40 mins.
Samples stored at 40 C. for 1 week after sterilization are in ( ) whereas samples after two months time point are in [ ].
N/A = not applicable
N/TRIS = No Tris Sterilized Disodium Pyrophosphate (Table 4):

There was no change in pH after sterilization and less than 0.1 pH unit change after storage for up to two months at 40° C. for all solutions.

There was less than 20% recovery of pyrophosphate after sterilization with all buffers at pH 6 and lower and less than 20% recovery with lactate with TRIS and with pyruvate at pH 7 and 8.

Recovery after sterilization increased with increasing pH, from pH 7-10, with all buffers.

Bicarbonate gave the highest recovery after sterilization at every pH from 7-10 and reached 99% at pH 10. Bicarbonate without TRIS gave higher recoveries than bicarbonate with TRIS at pH 7 and 8.

Recoveries after sterilization were similar for lactate with TRIS and pyruvate from pH 7-10.

Higher recoveries after sterilization were observed for citrate at pH 9 and 10, than with lactate with TRIS. Recoveries after sterilization were similar for lactate without TRIS and citrate, at pH 7 and 8.

Pyrophosphate was stable for 1 week at 40° C. with all buffers, from pH 7-10, except for lactate without TRIS at pH 7. Solutions with pH 4-6 were not tested after one week because of the low recoveries after sterilization.

TABLE 5

Recoveries of Tetrapotassium Pyrophosphate (Unsterilized)

| pH | Sod. Lac | Sod. BiC | Citrate | Pyruvate |
|---|---|---|---|---|
| 4 | 91 | N/A | 86 | 97 |
| 5 | 97 | N/A | 93 | 99 |
| 6 | 96 | N/A | 99 | 100 |
| 7 | 98 | 96 | 101 | 102 |
| 8 | 98 | 97 | 102 | 103 |
| 9 | 98 | 97 | 102 | 103 |
| 10 | 98 | 95 | 102 | 102 |

Reported values are the % recovery of the pyrophosphate
Values are rounded to the nearest whole numbers.
Results obtained before sterilization.
N/A = not applicable Unsterilized Tetrapotassium Pyrophosphate (Table 5):

Recoveries for tetrapotassium pyrophosphate were similar to the recoveries for disodium pyrophosphate for all buffers at all pH's.

TABLE 6

Recoveries of Tetrapotassium Pyrophosphate (Sterilized) and after Storage at 40° C.

| pH | Sod. Lac | Sod. BiC | Citrate | Pyruvate |
|---|---|---|---|---|
| 4 | 4 | N/A | 8 | 9 |
| 5 | 4 | N/A | 9 | 9 |
| 6 | 5 | N/A | 15 | 10 |
| 7 | 5 (9) | 55 (52) | 32 (32) | 9 (14) |
| 8 | 11 (12) | 71 (70) | 41 (41) | 11 (15) |
| 9 | 45 (44) | 91 (90) | 71 (71) | 54 (52) |
| 10 | 80 (77) | 97 (96) | 89 (90) | 83 (79) |

Reported values are the % recovery of the pyrophosphate
Values are rounded to the nearest whole numbers.
Samples sterilized at 121 C. for 40 mins.
Samples stored at 40 C. for 1 week after sterilization are in parenthesis.
N/A = not applicable
N/TRIS = No Tris Sterilized Tetrapotassium Pyrophosphate (Table 6):

There was no change in pH after sterilization and less than 0.1 pH unit change after storage for 1 week.

There was less than 20% recovery of pyrophosphate after sterilization with all buffers at pH 6 and lower, as was seen for sodium pyrophosphate.

Recovery after sterilization increased with increasing pH, from pH 7-10, with all buffers, as was seen with disodium phosphate.

Bicarbonate gave the highest recovery after sterilization at every pH from 7-10, as was seen with disodium pyrophosphate.

Pyrophosphate was stable for 1 week at 40° C. with all buffers, from pH 7-10. Solutions with pH 4-6 were not tested after one week because of the low recoveries after sterilization.

Conclusion:

There was no change in the pH of the solutions of either the sodium or potassium salts after sterilization and after storage for a week at 40° C. There was a substantial loss of pyrophosphate with both the sodium and potassium salts during sterilization, with all buffers, at pH 6 and lower. Both the sodium and potassium salts were the most stable during sterilization with bicarbonate at pH 9-10. Both the sodium and potassium salts remained unchanged on storage at 40° C. for 1 week, from pH 7-10, with all buffers.

It should be understood that various changes and modifications to the presently preferred embodiments described herein will be apparent to those skilled in the art. Such changes and modifications can be made without departing from the spirit and scope of the present subject matter and without diminishing its intended advantages. It is therefore intended that such changes and modifications be covered by the appended claims.

The invention is claimed as follows:

1. A heat sterilized solution comprising a pyrophosphate, a buffer comprising bicarbonate, and a pH greater than 7, wherein the bicarbonate buffer and the pH greater than 7 heat stabilize the pyrophosphate.

2. The solution of claim 1, wherein the pyrophosphate ranges from about 0.1 μM to about 1000 μM.

3. The solution of claim 1, wherein the solution is a concentrate.

4. The solution of claim 1, wherein the sterilization is performed by a technique selected from the group consisting of autoclave, steam and combinations thereof.

5. The solution of claim 1, wherein the pyrophosphate is selected from the group consisting of pyrophosphoric acid, salt of pyrophosphate and combinations thereof.

6. The solution of claim 1, wherein the pH is greater than 8.

7. The solution of claim 1, wherein the pH is greater than 9.

8. The solution of claim 1 further comprising a component selected from the group consisting of osmotic agents, electrolytes and combinations thereof.

9. The solution of claim 8, wherein the osmotic agent is selected from the group consisting of glucose, glucose polymers, glucose polymer derivatives, cyclodextrins, modified starch, hydroxyethyl starch, polyols, fructose, amino acids, peptides, proteins, amino sugars, glycerol, N-acetyl glucosamine (NAG) and combinations thereof.

10. The solution of claim 8, wherein the buffer further comprises a component selected from the group consisting of lactate, pyruvate, acetate, citrate, tris, amino acids, peptides, an intermediate of the KREBS cycle and combinations thereof.

11. The solution of claim 1 further comprising at least two parts housed separately and the pyrophosphate and the bicarbonate buffer are present with at least one of the parts and sterilized with said part.

12. The solution of claim 11, wherein the part comprising the pyrophosphate and the bicarbonate buffer has a pH greater than 8.

13. The solution of claim 11, wherein the part comprising the pyrophosphate and the bicarbonate buffer has a pH greater than 9.

14. The solution of claim 11, wherein electrolytes are balanced between the first part and the second part.

15. The solution of claim 1, wherein the solution is a dialysis solution.

16. A heat sterilized dialysis product comprising:
a first dialysis part comprising a dialysis component selected from the group consisting of osmotic agents, electrolytes and combinations thereof; and
a second dialysis part comprising pyrophosphate, bicarbonate and a pH greater than 7, wherein the bicarbonate and the pH greater than 7 heat stabilize the pyrophosphate.

17. The dialysis product of claim 16, wherein the pyrophosphate ranges from about 0.1 μM to about 1000 μM.

18. The dialysis product of claim 16, wherein the second dialysis part further comprises lactate.

19. The dialysis product of claim 16, wherein the second dialysis part further comprises a buffer selected from the group consisting of pyruvate, acetate, citrate, tris, amino acids, peptides, an intermediate of the KREBS cycle and combinations thereof.

20. The dialysis product of claim 16, wherein the sterilization is performed by a technique selected from the group consisting of autoclave, steam and combinations thereof.

21. The dialysis product of claim 16, wherein the pyrophosphate is selected from the group consisting of pyrophosphoric acid, salt of pyrophosphate and combinations thereof.

22. The dialysis product of claim 16, wherein the osmotic agent is selected from the group consisting of glucose, glucose polymers, glucose polymer derivatives, cyclodextrins, modified starch, hydroxyethyl starch, polyols, fructose, amino acids, peptides, proteins, amino sugars, glycerol, N-acetyl glucosamine (NAG) and combinations thereof.

23. The dialysis product of claim 16, wherein the electrolytes are selected from the group consisting of sodium, potassium, magnesium, calcium, chloride and combinations thereof.

24. The dialysis product of claim 16, wherein the second dialysis part further comprises an electrolyte selected from the group consisting of sodium, potassium, magnesium, calcium, chloride and combinations thereof.

25. The dialysis product of claim 16, wherein the pH of the second dialysis part is greater than 8.

26. The dialysis product of claim 16, wherein the pH of the second dialysis part is greater than 9.

* * * * *